US012447318B2

(12) United States Patent
Xiao et al.

(10) Patent No.: US 12,447,318 B2
(45) Date of Patent: Oct. 21, 2025

(54) BALLOON CATHETER

(71) Applicant: PIEDMONT MEDSYSTEMS (ZHUHAI) CO., LTD., Guangdong (CN)

(72) Inventors: Jiahua Xiao, Guangdong (CN); Yue Liu, Guangdong (CN)

(73) Assignee: PIEDMONT MEDSYSTEMS (ZHUHAI) CO., LTD., Zhuhai (CN)

( * ) Notice: Subject to any disclaimer, the term of this patent is extended or adjusted under 35 U.S.C. 154(b) by 692 days.

(21) Appl. No.: 17/596,243

(22) PCT Filed: Nov. 14, 2019

(86) PCT No.: PCT/CN2019/118314

§ 371 (c)(1),
(2) Date: Dec. 6, 2021

(87) PCT Pub. No.: WO2020/244154

PCT Pub. Date: Dec. 10, 2020

(65) Prior Publication Data

US 2022/0339412 A1 Oct. 27, 2022

(30) Foreign Application Priority Data

Jun. 6, 2019 (CN) ......................... 201910492068.9

(51) Int. Cl.
*A61M 25/10* (2013.01)

(52) U.S. Cl.
CPC .. *A61M 25/1011* (2013.01); *A61M 25/10185* (2013.11); *A61M 25/1025* (2013.01); *A61M 2025/1013* (2013.01)

(58) Field of Classification Search
CPC ........ A61M 25/1011; A61M 25/10185; A61M 25/1025; A61M 2025/1013; A61M 25/10; A61M 2025/1068; A61M 2025/1079; A61M 2025/1075; A61B 2018/00255; A61F 2007/0054; A61F 2007/126; A61F 7/12
See application file for complete search history.

(56) References Cited

U.S. PATENT DOCUMENTS 5,496,271 A * 3/1996 Burton ............... A61B 18/1815 604/113
6,471,672 B1 * 10/2002 Brown ............... A61M 25/1011 604/101.02

(Continued)

FOREIGN PATENT DOCUMENTS

CN 101822866 A 9/2010
CN 106102816 A 11/2016

(Continued)

OTHER PUBLICATIONS

JP2021-572504A Japanese Office Action with English Translation dated Nov. 1, 2022, 7 pages.

(Continued)

*Primary Examiner* — Shaun L David
*Assistant Examiner* — Rachael L Geiger
(74) *Attorney, Agent, or Firm* — Maschoff Brennan

(57) ABSTRACT

A balloon catheter includes a catheter and a balloon body sleeved on the catheter. The balloon body includes an inner layer balloon and an outer layer balloon. The inner layer balloon and the outer layer balloon are directly wrapped and fixed on the catheter. The inner layer balloon is inside the outer layer balloon. A medium channel is formed between the inner layer balloon and the outer layer balloon. An outer layer medium inlet hole and a medium backflow hole are both in communication with the medium channel. A medium can flow in the medium channel between the inner layer balloon and the outer layer balloon, the medium flows into the medium channel through the outer layer medium inlet hole, and then the medium in the medium channel flows out through the medium backflow hole to implement circulation.

5 Claims, 3 Drawing Sheets

(56) References Cited

U.S. PATENT DOCUMENTS

| | | | | |
|---|---|---|---|---|
| 7,144,407 | B1 | 12/2006 | Lasersohn | |
| 9,174,030 | B2 | 11/2015 | Boatman | |
| 11,911,581 | B1 * | 2/2024 | Golshan | A61B 17/12109 |
| 2002/0045925 | A1 | 4/2002 | Keller et al. | |
| 2012/0226230 | A1 * | 9/2012 | Gerrans | A61B 5/4839<br>604/103.01 |
| 2016/0339204 | A1 | 11/2016 | Williams et al. | |
| 2018/0344234 | A1 * | 12/2018 | McKinney | A61M 25/0032 |

FOREIGN PATENT DOCUMENTS

| | | | |
|---|---|---|---|
| CN | 106880400 | A | 6/2017 |
| CN | 208541677 | U | 2/2019 |
| CN | 110115798 | A | 8/2019 |
| EP | 0379794 | A1 | 8/1990 |
| EP | 2110151 | A1 | 10/2009 |
| JP | 2-283379 | A | 11/1990 |
| JP | 2011-206208 | A | 10/2011 |
| WO | 0112061 | A1 | 2/2001 |
| WO | 2020244154 | A | 12/2020 |

OTHER PUBLICATIONS

PCT/CN2019/118314 International Search Report dated Mar. 12, 2020, 3 pages (English translation).
PCT/CN2019/118314 Written Opinion dated Mar. 12, 2020, 5 pages (English translation).
PCT/CN2019/118314 Extended European Search Report dated Jun. 3, 2022, 8 pages.

* cited by examiner

BALLOON CATHETER

CROSS-REFERENCE

This application is the National Stage of, and therefore claims the benefit of and priority to, International Application No. PCT/CN2019/118314, filed on Nov. 14, 2019, entitled "Balloon Catheter," which was published as International Publication No. WO 2020/244154 A1 on Dec. 10, 2020, and which claims priority to Chinese patent application No. 201910492068.9, entitled "BALLOON CATHETER," filed with the China National Intellectual Property Administration on Jun. 6, 2019, the disclosures of which are hereby incorporated by reference in their entireties.

TECHNICAL FIELD

The present invention relates to the field of medical device technologies, and specifically to a balloon catheter.

BACKGROUND

A balloon catheter is a terminal device for interventional procedures, and is mainly used in angioplasty, cardiovascular treatment, stent delivery, lumen dilation, tracheal and esophageal dilatation and treatment, high pressure dilation, treatment of neurovascular occlusion, and the like. A balloon catheter is inserted into blood vessels, lumen, trachea, esophagus, urethra, and the like, and a balloon is used for support. The flow distribution and flow rate distribution of a medium in the balloon during the treatment have a relatively large impact on the treatment effect.

For a balloon catheter in the prior art, in a pressurized state, a medium flows through a catheter to enter a balloon cavity from an inlet and flows back through an outlet to complete circulation. The position of the inlet for the medium inside the balloon affects the flow rate distribution of the medium on the inner surface of the balloon. Due to the characteristics of the flow of the medium, when the medium is in contact with the inner surface of the balloon for heat exchange, there is a relatively small amount of effective heat exchange medium, resulting in incomplete heat exchange and therefore an inadequate therapeutic effect.

SUMMARY

An objective of the present invention is to provide a balloon catheter, to solve the technical problem of incomplete heat exchange of a heat exchange medium in the prior art.

To achieve the foregoing objective, the technical solution adopted in the present invention is as follows: A balloon catheter is provided, including a catheter and a balloon body sleeved on the catheter, where the balloon body includes an inner layer balloon and an outer layer balloon, the inner layer balloon and the outer layer balloon are both directly wrapped and fixed on the catheter, the inner layer balloon is located inside the outer layer balloon, a medium channel is formed between the inner layer balloon and the outer layer balloon, and an outer layer medium inlet hole and a medium backflow hole both in communication with the medium channel are provided in the catheter.

Further, an inner layer medium inlet hole in communication with the inner layer balloon is further provided in the catheter.

Further, a medium inlet tube and a medium backflow tube are provided in the catheter, the inner layer medium inlet hole and the outer layer medium inlet hole are both in communication with the medium inlet tube, and the medium backflow tube is in communication with the medium backflow hole.

Further, a control valve is disposed on the medium inlet tube, and the control valve is located between the inner layer medium inlet hole and the outer layer medium inlet hole.

Further, a medium inlet tube, a medium backflow tube, and an inner layer medium tube are disposed in the catheter, the inner layer medium inlet hole is in communication with the inner layer medium tube, the outer layer medium inlet hole is in communication with the medium inlet tube, and the medium backflow tube is in communication with the medium backflow hole.

Further, an end of the medium inlet tube is a catheter terminal end, the outer layer medium inlet hole is located at one end of the outer layer balloon away from the catheter terminal end, and the inner layer medium inlet hole is located on a side of the outer layer medium inlet hole close to the catheter terminal end.

Further, the medium backflow hole is located at the other end of the outer layer balloon close to the catheter terminal end.

Further, a guidewire cavity is further disposed in the catheter.

Further, the guidewire cavity is slidably connected to the catheter, and an end of the guidewire cavity away from a catheter terminal end is fixedly connected to an end of the outer layer balloon away from the catheter terminal end.

Further, a marking ring is disposed inside the inner layer balloon or the outer layer balloon.

The beneficial effects of the balloon catheter provided in the present invention are as follows: Compared with the prior art, in the balloon catheter in the present invention, the double-layer balloon body is provided, so that a medium can flow in the medium channel between the inner layer balloon and the outer layer balloon, the medium flows into the medium channel through the outer layer medium inlet hole, and then the medium in the medium channel flows out through the medium backflow hole to implement circulation. In this way, more medium can exchange heat on the inner surface of the outer layer balloon and the flow rate distribution is relatively uniform, to increase the flowing quality of the medium on the surface of the balloon body, thereby improving the heat exchange efficiency.

BRIEF DESCRIPTION OF THE DRAWINGS

To describe the technical solutions in specific embodiments of the present invention or the prior art more clearly, the following briefly introduces the accompanying drawings required for describing the specific embodiments or the prior art. Apparently, the accompanying drawings in the following description show some embodiments of the present invention, and a person of ordinary skill in the art may still derive other drawings from these accompanying drawings without creative efforts.

REFERENCE NUMERALS

1. catheter; 2. balloon body; 11. outer layer medium inlet hole; 12. medium backflow hole; 13. inner layer medium inlet hole; 14. medium inlet tube; 15. medium backflow tube; 16. guidewire cavity; 17. catheter terminal end; 18. fixing end portion; 19. slidable tube body; 141. control valve; 21. inner layer balloon; 22. outer layer balloon; 23. medium channel; and 24. marking ring.

DETAILED DESCRIPTION

The following clearly and completely describes the technical solutions of the present invention with reference to the accompanying drawings. Apparently, the described embodiments are merely some rather than all of the embodiments of the present invention. All other embodiments obtained by persons of ordinary skill in the art based on the embodiments of the present invention without creative efforts shall fall within the protection scope of the present invention.

In the description of the present invention, it needs to be understood that orientation or location relationships indicated by terms "center", "up", "down", "left", "right", "vertical", "horizontal", "inside", and "outside" are based on orientation or location relationships shown in the accompanying drawings, and are only used to facilitate description of the present invention and simplify description, but are not used to indicate or imply that the apparatuses or elements must have specific orientations or are constructed and operated by using specific orientations, and therefore, cannot be understood as a limitation to the present invention. In addition, the terms "first", "second", and "third" are used only for description, but are not intended to indicate or imply relative importance.

In the description of the present invention, it needs to be noted that unless otherwise expressly specified and defined, "mounted", "connected", and "connection", should be understood in a broad sense, for example, fixedly connected, detachably connected or integrally connected; or mechanically connected or electrically connected; or connected directly or indirectly through an intermediate, or two elements communicated internally. For a person of ordinary skill in the art, specific meanings of the terms in the present invention should be understood according to specific conditions.

In addition, the technical features involved in different embodiments of the present invention described below can be combined with each other as long as they do not constitute a conflict between them.

Embodiment 1

Figure 1:
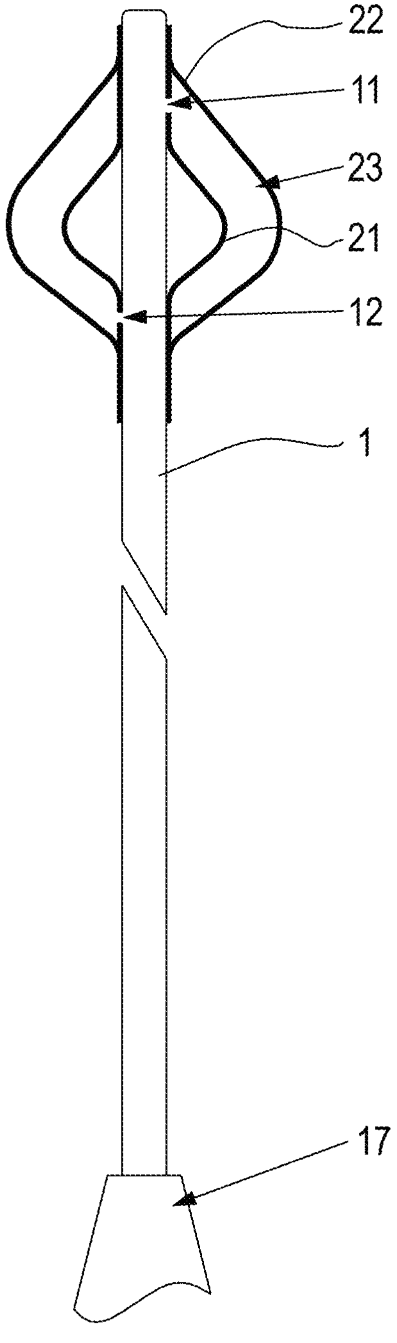
FIG. 1 is a schematic structural diagram of a balloon catheter according to an embodiment of the present invention.
Figure 2:
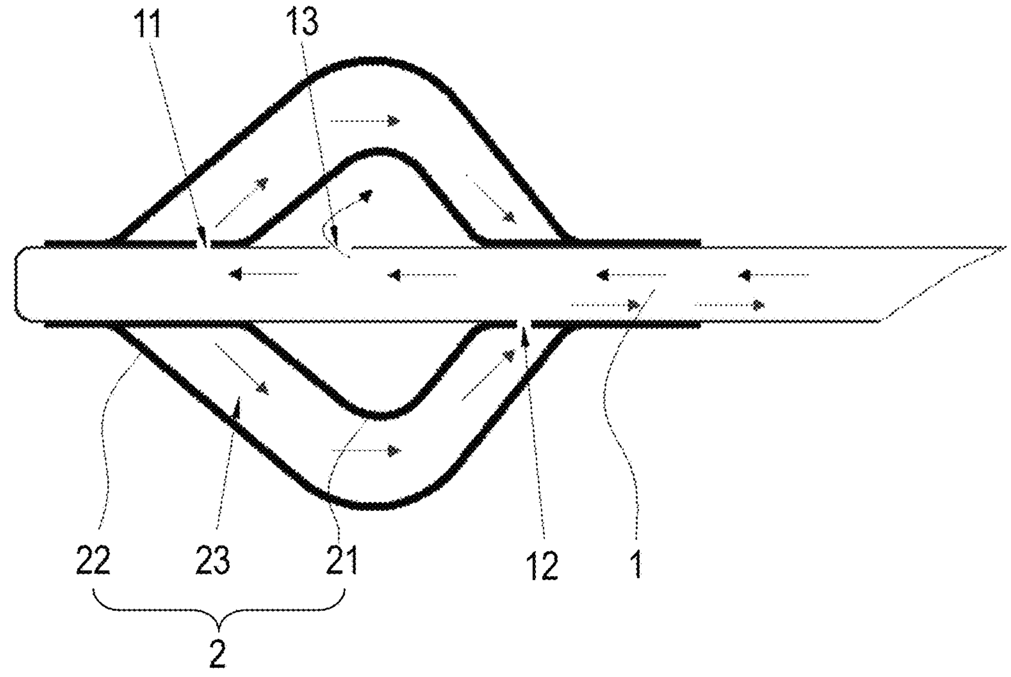
FIG. 2 is a schematic diagram of the flow of a medium in a balloon catheter according to an embodiment of the present invention.

Referring to FIG. 1 and FIG. 2 together, a balloon catheter provided in the present invention is described. The balloon catheter includes a catheter 1 and a balloon body 2 sleeved on the catheter 1. The balloon body 2 includes an inner layer balloon 21 and an outer layer balloon 22. The inner layer balloon 21 and the outer layer balloon 22 are both directly wrapped and fixed on the catheter 1. The inner layer balloon 21 is located inside the outer layer balloon 22. A medium channel 23 is formed between the inner layer balloon 21 and the outer layer balloon 22. An outer layer medium inlet hole 11 and a medium backflow hole 12 both in communication with the medium channel 23 are provided in the catheter 1.

In the balloon catheter provided in the present invention, compared with the prior art, the double-layer balloon body 2 is provided, so that a medium can flow in the medium channel 23 between the inner layer balloon 21 and the outer layer balloon 22, the medium flows into the medium channel 23 through the outer layer medium inlet hole 11, and then the medium in the medium channel 23 flows out through the medium backflow hole 12 to implement circulation of the medium. In this way, more medium can exchange heat on the inner surface of the outer layer balloon 22 and the flow rate distribution is relatively uniform, to increase the flowing quality of the medium on the surface of the balloon body 2, thereby improving the heat exchange efficiency.

Specifically, the balloon body 2 is directly sleeved on the catheter 1. The balloon body 2 is generally disposed at a terminal end of the catheter 1. The balloon body 2 is expandable under the filling of the medium, to fill and support narrow places such as blood vessels, trachea and urethra. Middle parts of the inner layer balloon 21 and the outer layer balloon 22 can both swell after the medium is filled, the inner layer balloon 21 and the outer layer balloon 22 are generally the same in shape, and there is the same distance between the outer surface of the inner layer balloon 21 and the inner surface of the outer layer balloon 22, to ensure that the entire medium channel 23 has the same channel size, thereby ensuring relatively uniform flow rate distribution of the medium. Certainly, according to an actual case and specific requirements, in other embodiments of the present invention, the inner layer balloon 21 and the outer layer balloon 22 may have different shapes. This is not uniquely limited herein.

Figure 3:
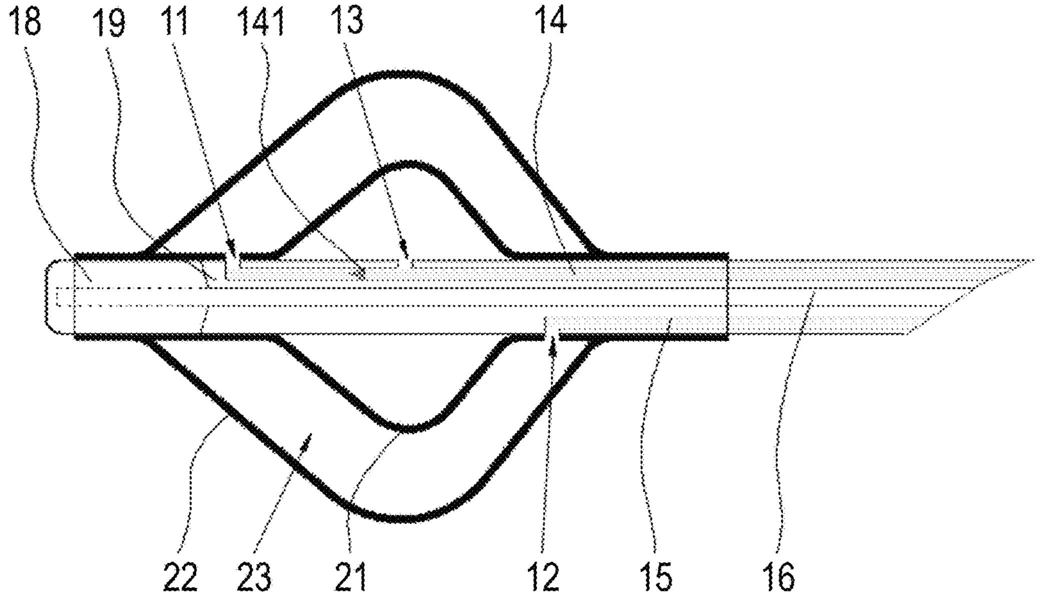
FIG. 3 is a schematic structural sectional view 1 of a balloon catheter according to an embodiment of the present invention.

Further, referring to FIG. 1 to FIG. 3 together, in a specific implementation of the balloon catheter provided in the present invention, and an inner layer medium inlet hole 13 in communication with the inner layer balloon 21 is further provided in the catheter 1. Specifically, the medium may flow through the inner layer medium inlet hole 13 into the inner layer balloon 21, to ensure that the medium can fill the inner layer balloon 21. The medium filling the inner layer balloon 21 and the medium filling the outer layer balloon 22 are generally the same medium. A through hole is directly provided in a sidewall of the catheter 1, so that the medium located in the catheter 1 may flow into the inner layer balloon 21.

Preferably, there may be a plurality of inner layer medium inlet holes 13, a plurality of outer layer medium inlet holes 11, and a plurality of medium backflow holes 12, which are evenly distributed in the sidewall of the catheter 1, so that the speed at which the medium in the catheter 1 flows into the balloon body 2 can be increased, and it can be ensured that the flow rate of the medium in the outer layer balloon 22 is uniform.

Further, referring to FIG. 1 to FIG. 3, in a specific implementation of the balloon catheter provided in the present invention, a medium inlet tube 14 and a medium backflow tube 15 are provided in the catheter 1. The inner layer medium inlet hole 13 and the outer layer medium inlet hole 11 are both in communication with the medium inlet tube 14. The medium backflow tube 15 is in communication with the medium backflow hole 12. Specifically, the medium inlet tube 14 and the medium backflow tube 15 are two separate tube bodies, and the medium inlet tube 14 and the medium backflow tube 15 are both in direct communication with an outer side of the catheter 1. The medium inlet tube 14 may be in direct communication with the inner layer medium inlet hole 13 and the outer layer medium inlet hole 11. Both the medium in the inner layer balloon 21 and the medium in the outer layer balloon 22 are transported through the medium inlet tube 14. The medium in the outer layer balloon 22 flows through the medium channel 23 and flows out through the medium backflow hole 12 to the medium backflow tube 15 to implement the circulation of all the medium. Certainly, according to an actual case and specific requirements, in other embodiments of the present invention, the medium inlet tube 14 may be only in communication with the outer layer medium inlet hole 11. The medium required for the inner layer balloon 21 may be directly transported by a separate tube body. This is not uniquely limited herein.

Further, referring to FIG. 1 to FIG. 3, in a specific implementation of the balloon catheter provided in the present invention, a control valve 141 is disposed on the medium inlet tube 14. The control valve 141 is located between the inner layer medium inlet hole 13 and the outer layer medium inlet hole 11. Specifically, the control valve 141 can control the flow direction of the medium, to ensure that the medium first flows from the medium inlet tube 14 to the inner layer balloon 21, and then, when the pressure in the inner layer balloon 21 is greater than a threshold, the control valve 141 is opened to allow the medium to flow to the outer layer medium inlet hole 11 to fill the outer layer balloon 22, thereby avoiding the problem that the medium directly enters the outer layer balloon 22 for circulation and fails to fill the inner layer balloon 21.

Further, referring to FIG. 1 to FIG. 3, in a specific implementation of the balloon catheter provided in the present invention, the control valve 141 is a throttle check valve. Specifically, a throttle valve and a check valve may be combined into a throttle check valve. The throttle valve can open under the action of pressure, and the throttle valve allows one direction, so that the medium can only flow through the inner layer medium inlet hole 13 to enter the outer layer medium inlet hole 11. The backflow of the medium can be effectively avoided. The throttle check valve can ensure the use stability of the balloon catheter, to ensure that the medium fills the inner layer balloon 21 before the medium can fill the outer layer balloon 22, thereby avoiding direct backflow of the medium in the outer layer balloon 22.

Further, referring to FIG. 1 to FIG. 3, in a specific implementation of the balloon catheter provided in the present invention, the medium inlet tube 14 and the medium backflow tube 15 are located on two opposite sides on an inner side of the catheter 1. Specifically, the medium inlet tube 14 and the medium backflow tube 15 are located on the inner side of the catheter 1, and the medium inlet tube 14 and the medium backflow tube 15 are both located on a side of the catheter 1 close to a sidewall, so that connections between the inner layer medium inlet hole 13, the outer layer medium inlet hole 11, and the medium backflow hole 12 can be conveniently implemented, and the connections can be implemented by directly opening through holes in the medium inlet tube 14 or the medium backflow tube 15. Certainly, according to an actual case and specific requirements, in other embodiments of the present invention, the medium inlet tube 14 and the medium backflow tube 15 may be directly filled inside the catheter 1, or the medium inlet tube 14 and the medium backflow tube 15 may be tubes independent of the catheter 1, or all channels are designed into a composite multi-cavity tube. This is not uniquely limited herein.

Further, referring to FIG. 1 to FIG. 3, in a specific implementation of the balloon catheter provided in the present invention, an end of the medium inlet tube 14 is a catheter terminal end 17. The outer layer medium inlet hole 11 is located at one end of the outer layer balloon 22 away from the catheter terminal end 17. The inner layer medium inlet hole 13 is located on a side of the outer layer medium inlet hole 11 close to the catheter terminal end 17. Specifically, an end of the catheter 1 is the catheter terminal end 17. The catheter terminal end 17 may be an inlet end for the medium and an insertion end for a guidewire. The inner layer medium inlet hole 13 is located near the catheter terminal end 17. That is, the medium fills the inner layer balloon 21 before the medium can fill the outer layer balloon 22, to avoid that all the medium flows into the outer layer balloon 22 to flow out through the medium backflow hole 12, thereby ensuring that both the inner layer and the outer layer of the balloon body 2 can be filled. Certainly, according to an actual case and specific requirements, in other embodiments of the present invention, when an inner layer medium tube is separately disposed, the positions of the inner layer medium inlet hole 13 and the outer layer medium inlet hole 11 may be adjusted as required. This is not uniquely limited herein.

Further, referring to FIG. 1 to FIG. 3, in a specific implementation of the balloon catheter provided in the present invention, the medium backflow hole 12 is located at the other end of the outer layer balloon 22 close to the catheter terminal end 17. Specifically, the medium backflow hole 12 and the outer layer medium inlet hole 11 are separately are located at two opposite ends of the outer layer balloon 22, to ensure that the medium can form complete circulation in the outer layer balloon 22, thereby avoiding that the medium fails to completely fill the outer layer balloon 22, so that it is avoided that the support and fixation are inadequate because the outer layer balloon 22 fails to fully expand. Certainly, according to an actual case and specific requirements, in other embodiments of the present invention, a throttle valve may be disposed at the medium backflow hole 12. The medium can flow back through the medium backflow hole 12 only when the pressure in the outer layer balloon 22 is greater than a particular degree. This is not uniquely limited herein.

Further, referring to FIG. 1 to FIG. 3, in a specific implementation of the balloon catheter provided in the present invention, a guidewire cavity 16 is further disposed in the catheter 1. Specifically, the guidewire cavity 16 has assistant functions such as threading a guidewire and introducing a liquid. The guidewire cavity 16 is usually located at the middle part of the catheter 1, the medium inlet tube 14 and the medium backflow tube 15 are both located on two sides of the guidewire cavity 16, and a space for the guidewire cavity 16 is reserved in the catheter 1, to allow for increased applicability and increased functionality of the balloon catheter.

Figure 4:
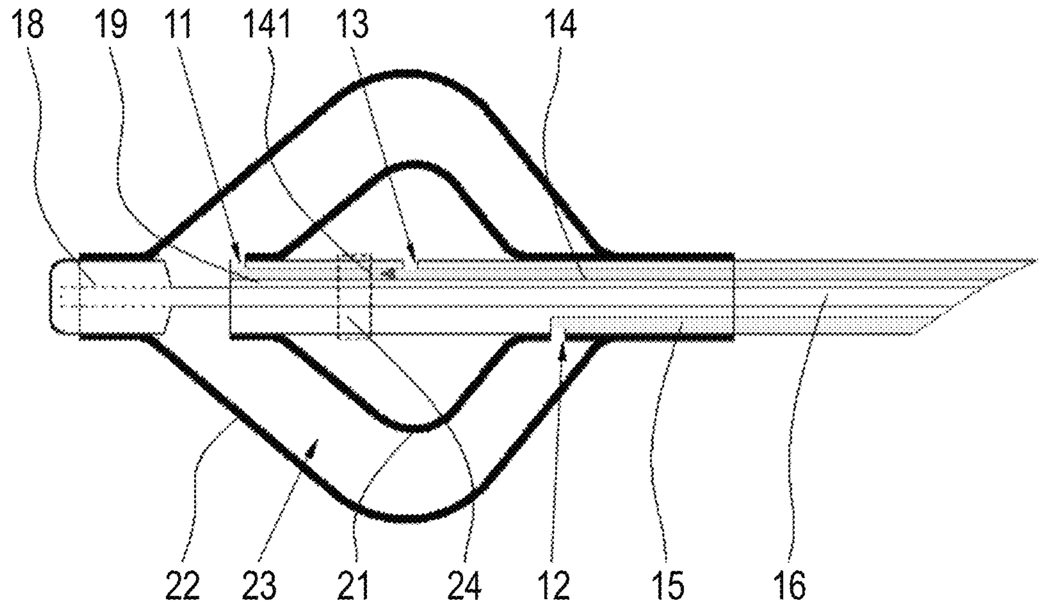
FIG. 4 is a schematic structural sectional view 2 of a balloon catheter according to an embodiment of the present invention.

Further, referring to FIG. 3 and FIG. 4, in a specific implementation of the balloon catheter provided in the present invention, the guidewire cavity 16 is slidably connected to the catheter 1, and an end of the guidewire cavity 16 away from the catheter terminal end 17 is fixedly connected to one end of the outer layer balloon 22 away from the catheter terminal end 17. Specifically, the catheter 1 has a long tube body. The guidewire cavity 16 is provided inside the catheter 1. The guidewire cavity 16 may slide relatively inside the catheter 1. The end of the guidewire cavity 16 away from the catheter terminal end 17 may be directly fixedly connected to the end of the outer layer balloon 22 away from the catheter terminal end 17. The other end of the outer layer balloon 22 close to the catheter terminal end 17 is fixedly connected to the catheter 1, so that a spacing between two ends of the outer layer balloon 22 can be changed. When the spacing between the two ends of the outer layer balloon 22 increases, the outer layer balloon 22 has an increased side length and is attached to the outer side of the catheter 1, to further facilitate interventional treatment with the entire balloon catheter. When the spacing between the two ends of the outer layer balloon 22 decreases, the outer layer balloon 22 can be filled to provide support.

Further, referring to FIG. 3 and FIG. 4, in a specific implementation of the balloon catheter provided in the present invention, a marking ring 24 is disposed inside the inner layer balloon 21 or the outer layer balloon 22. Specifically, the marking ring 24 is disposed inside the balloon body 2 and may mark the position of the balloon body 2 to facilitate observation from outside. The marking ring 24 is generally disposed inside the inner layer balloon 21 or the outer layer balloon 22. The marking ring 24 is annularly disposed on the outer side of the catheter 1 to implement the fixation of the marking ring 24. The material of the marking ring 24 is usually a platinum-iridium alloy or another alloy material that can implement marking.

Embodiment 2

In another embodiment of the present invention, referring to FIG. 1 to FIG. 3, differences between this embodiment and Embodiment 1 are as follows: A medium inlet tube 14, a medium backflow tube 15, and an inner layer medium tube (not shown in the figure) are disposed in the catheter 1, the inner layer medium inlet hole 13 is in communication with the inner layer medium tube, the outer layer medium inlet hole 11 is in communication with the medium inlet tube 14, and the medium backflow tube 15 is in communication with the medium backflow hole 12. Specifically, the medium inlet tube 14, the medium backflow tube 15, and the inner layer medium tube are all separate tube bodies, and the inner layer medium inlet hole 13 is in communication with the inner layer medium tube. Because the inner layer medium tube and the medium inlet tube 14 are two separate tube bodies, it is not necessary to arrange the control valve 141 to control the flow rate, so that the control method is simpler, and a medium can be directly transported for the inner layer balloon 21 and the outer layer balloon 22. The medium in the outer layer balloon 22 flows through the medium channel 23 and flows out through the medium backflow hole 12 to the medium backflow tube 15 to implement the circulation of all the medium.

Obviously, the foregoing embodiments are merely examples for clear description, rather than a limitation to implementations. For a person of ordinary skill in the art, other changes or variations in different forms may also be made based on the foregoing description. All implementations cannot and do not need to be exhaustively listed herein. Obvious changes or variations that are derived there from still fall within the protection scope of the invention of the present invention.

The invention claimed is:

1. A balloon catheter, comprising:

a catheter; and a balloon body sleeved on the catheter, wherein:

the balloon body comprises an inner layer balloon and an outer layer balloon which are both directly wrapped and fixed on the catheter;

the inner layer balloon is located inside the outer layer balloon such that a medium channel is formed between the inner and outer layer balloons for circulation flow of a heat-exchange medium;

the catheter includes:

an outer layer medium inlet hole and a medium backflow hole both in communication with the medium channel;

an inner layer medium inlet hole in communication with the inner layer balloon;

a medium inlet tube; and a medium backflow tube;

the inner and outer layer medium inlet holes are both in communication with the medium inlet tube;

the medium backflow tube is in communication with the medium backflow hole;

an end of the medium inlet tube is a catheter proximal terminal end;

the inner layer medium inlet hole is located on a side of the outer layer medium inlet hole close to the catheter proximal terminal end;

the outer layer medium inlet hole is located at one end of the outer layer balloon away from the catheter proximal terminal end;

the medium backflow hole is located at the other end of the outer layer balloon close to the catheter proximal terminal end;

a control valve is disposed on the medium inlet tube between the inner and outer layer medium inlet holes; and the control valve is a throttle check valve that can be opened under the action of pressure and is configured to control the flow direction of the heat-exchange medium to ensure that the heat-exchange medium first flows from the medium inlet tube into the inner layer balloon through the inner layer medium inlet hole, and then, when the pressure in the inner layer balloon becomes greater than a threshold, the control valve opens to allow the heat-exchange medium to flow from the medium inlet tube into the medium channel between the inner and outer layer balloons through the outer layer medium inlet hole and then flow back through the medium backflow hole, so as to realize the circulation flow of the heat-exchange medium in the medium channel for convective heat transfer.

2. The balloon catheter according to claim 1, wherein a guidewire tube is further disposed in the catheter.

3. The balloon catheter according to claim 2, wherein the guidewire tube is slidably connected to the catheter, and an end of the guidewire tube away from a catheter proximal terminal end is fixedly connected to an end of the outer layer balloon away from the catheter terminal end.

4. The balloon catheter according to claim 1, wherein a marking ring is disposed inside the inner layer balloon or the outer layer balloon.

5. A method for using the balloon catheter according to claim 1, the method comprising:

supplying a heat-exchange medium from the medium inlet tube to the inner layer balloon through the inner layer medium inlet hole; and when the pressure in the inner layer balloon becomes greater than a threshold and the control valve is opened under the action of pressure, supplying the heat-exchange medium from the medium inlet tube into the medium channel between the inner layer balloon and the outer layer balloon through the outer layer medium inlet hole and making the heat-exchange medium flow back through the medium backflow hole, so as to realize the circulation flow of the heat-exchange medium in the medium channel for convective heat transfer.

* * * * *